US011110997B2

(12) United States Patent
Jia et al.

(10) Patent No.: US 11,110,997 B2
(45) Date of Patent: Sep. 7, 2021

(54) SYSTEM FOR MEASURING MECHANICAL PROPERTIES OF SEA FLOOR SEDIMENTS AT FULL OCEAN DEPTHS

(71) Applicant: OCEAN UNIVERSITY OF CHINA, Shandong (CN)

(72) Inventors: Yonggang Jia, Shandong (CN); Hong Zhang, Shandong (CN); Xiaolei Liu, Shandong (CN); Hongxian Shan, Shandong (CN)

(73) Assignee: OCEAN UNIVERSITY OF CHINA, Qingdao (CN)

( * ) Notice: Subject to any disclaimer, the term of this patent is extended or adjusted under 35 U.S.C. 154(b) by 0 days.

(21) Appl. No.: 16/632,509

(22) PCT Filed: Apr. 1, 2019

(86) PCT No.: PCT/CN2019/080722
§ 371 (c)(1),
(2) Date: Jan. 20, 2020

(87) PCT Pub. No.: WO2020/082690
PCT Pub. Date: Apr. 30, 2020

(65) Prior Publication Data
US 2020/0355590 A1     Nov. 12, 2020

(30) Foreign Application Priority Data
Oct. 24, 2018   (CN) ......................... 201811246959.8

(51) Int. Cl.
*B63B 35/00*    (2020.01)
*A47B 91/02*    (2006.01)
(Continued)

(52) U.S. Cl.
CPC .............. *B63B 35/00* (2013.01); *A47B 91/02* (2013.01); *B63B 1/30* (2013.01); *B63B 22/00* (2013.01);
(Continued)

(58) Field of Classification Search
CPC .. G01N 3/30; G01N 3/00; G01N 3/42; G01N 11/12; G01N 11/14; G01N 33/24;
(Continued)

(56) References Cited

U.S. PATENT DOCUMENTS

2011/0280100 A1\* 11/2011 Thomas ............... G01V 1/3808
                                                                  367/16
2012/0289103 A1\* 11/2012 Hudson ................... F42B 19/01
                                                                  440/38
(Continued)

FOREIGN PATENT DOCUMENTS

CN          2704680 Y  \*  6/2005
CN          2704680 Y      6/2005
(Continued)

*Primary Examiner* — Marrit Eyassu
(74) *Attorney, Agent, or Firm* — Berenato & White, LLC

(57) ABSTRACT

The present invention discloses a system for measuring the mechanical properties of sea floor sediments at full ocean depth. The system includes an overwater monitoring unit and an underwater measurement device, where the underwater measurement device includes an observation platform and a measuring mechanism; the observation platform includes a frame-type body and a floating body, a wing panel, a floating ball cabin, a leveling mechanism, a counterweight, and a release mechanism mounted on the frame-type body; the floating ball cabin seals a circuit system; the leveling mechanism adjusts the underwater measurement device horizontally on the sea floor when the frame-type body reaches the sea floor; the release mechanism discards the counterweight for recovery of the unit after the underwater measurement device completes the underwater opera-
(Continued)

tion; the measuring mechanism includes at least one of a cone penetration measuring mechanism, a spherical penetration measuring mechanism, and a vane shear measuring mechanism, or a sampling mechanism.

12 Claims, 10 Drawing Sheets

(51) Int. Cl.
| | |
|---|---|
| B63B 1/30 | (2006.01) |
| B63B 22/00 | (2006.01) |
| E02D 1/02 | (2006.01) |
| E02D 1/04 | (2006.01) |
| E21B 15/02 | (2006.01) |
| E21B 25/16 | (2006.01) |
| E21B 25/18 | (2006.01) |
| E21B 49/00 | (2006.01) |
| F16M 7/00 | (2006.01) |
| G01L 7/00 | (2006.01) |
| G01N 3/30 | (2006.01) |
| G01N 3/42 | (2006.01) |
| G01N 11/12 | (2006.01) |
| G01N 11/14 | (2006.01) |
| G01N 33/24 | (2006.01) |
| G01S 1/70 | (2006.01) |
| G01V 1/38 | (2006.01) |
| G01V 9/00 | (2006.01) |
| H04B 11/00 | (2006.01) |
| H04B 13/02 | (2006.01) |

(52) U.S. Cl.
CPC ............... *E02D 1/025* (2013.01); *E02D 1/04* (2013.01); *E21B 15/02* (2013.01); *E21B 25/16* (2013.01); *E21B 25/18* (2013.01); *E21B 49/001* (2013.01); *F16M 7/00* (2013.01); *G01L 7/00* (2013.01); *G01N 3/30* (2013.01); *G01N 3/42* (2013.01); *G01N 11/12* (2013.01); *G01N 11/14* (2013.01); *G01N 33/24* (2013.01); *G01S 1/70* (2013.01); *G01V 1/38* (2013.01); *G01V 9/00* (2013.01); *H04B 11/00* (2013.01); *H04B 13/02* (2013.01); *B63B 2207/02* (2013.01); *G01N 2203/0032* (2013.01)

(58) Field of Classification Search
CPC ... G01N 2203/0032; G01N 2001/1031; G01N 1/12; A47B 91/02; B63B 1/30; B63B 22/00; B63B 35/00; B63B 22/003; B63B 2207/02; E02D 1/025; E02D 1/04; E21B 15/02; E21B 25/16; E21B 25/18; E21B 49/001; F16M 7/00; G01L 7/00; G01S 1/70; G01V 1/38; G01V 9/00; H04B 11/00; H04B 13/02
See application file for complete search history.

(56) References Cited

U.S. PATENT DOCUMENTS

| | | | |
|---|---|---|---|
| 2018/0141628 A1* | 5/2018 | Rokkan | B63B 27/16 |
| 2018/0222560 A1* | 8/2018 | Postic | B63G 8/001 |

FOREIGN PATENT DOCUMENTS

| | | | | |
|---|---|---|---|---|
| CN | 102320347 A | | 1/2012 | |
| CN | 102320347 B | * | 4/2014 | |
| CN | 106707361 A | | 5/2017 | |
| CN | 106841311 A | * | 6/2017 | ........... G01V 1/3852 |
| CN | 106841311 A | | 6/2017 | |
| CN | 108146581 A | | 6/2018 | |
| CN | 207991994 U | | 10/2018 | |
| CN | 109094742 A | | 12/2018 | |
| CN | 109297803 A | | 2/2019 | |
| KR | 20150000168 A | | 1/2015 | |

* cited by examiner

SYSTEM FOR MEASURING MECHANICAL PROPERTIES OF SEA FLOOR SEDIMENTS AT FULL OCEAN DEPTHS

CROSS-REFERENCE TO RELATED APPLICATIONS AND CLAIM TO PRIORITY

This application is a national stage application of International Application No. PCT/CN2019/080722 filed Apr. 1, 2019, which claims priority to Chinese Patent Application No. 201811246959.8 filed Oct. 24, 2018, the disclosures of which are incorporated herein by reference and to which priority is claimed.

TECHNICAL FIELD

The invention relates to the technical field of ocean observation, and particularly relates to a system for measuring the mechanical properties of sea floor sediments.

BACKGROUND

These days, marine research has entered the era of full ocean depth exploration. The deepest regions of the ocean on Earth are waters at a depth of around 6,000 m to 11,000 m, known by scientists as "Hadal Trenches". These regions are mainly distributed on the edge of continents and are composed of trenches. Although they only account for 1%-2% of the global sea floor area, their vertical depth accounts for 45% of the full ocean depth, which is of great significance in marine ecosystems. At present, research regarding "Hadal Trenches" has become the latest frontier of marine research, which also means that marine science has entered the era of full-ocean-depth scientific research. Consequently, numerous marine projects based on sea floor soil have emerged. It is extremely important to accurately obtain the mechanical properties of sea floor sediments for deep-ocean scientific research, resource and energy development engineering activities, and marine security and national defense engineering.

As a result, devices for measuring the mechanical properties of sea floor sediments are continuously being developed, and the working area is continuously expanding from shallow ocean to deep ocean. Existing measurement devices are mainly launched with cables, which can achieve long-term stable observation on the sea floor at depths of less than 6,000 m. However, as the working water depth increases, especially when the observation area is a "Hadal Trench", the work cannot be carried out with such devices due to the limitation of the length of the geological cables on the scientific research vessel. In order to achieve the in-situ detection of deep-ocean sediments, existing in-situ measurement devices for measuring sediment mechanical properties with a working water depth greater than 6,000 m, are carried out by a submersible (such as the "Jiaolong"). However, it is expensive to use submersibles, and it is impossible to use submersibles for long-term continuous operation. Therefore, it is difficult to promote the application of submersibles for such tasks.

SUMMARY

An objective of the invention is to provide a system for measuring the mechanical properties of sea floor sediments at full ocean depth. The underwater measurement device of the measurement system is launched without a cable, and can measure the mechanical properties of the sea floor sediments at any depth. Moreover, the underwater measurement device can realize automatic recovery, reducing the research cost.

To solve the above technical problems, the invention adopts the following technical solutions.

A system for measuring the mechanical properties of sea floor sediments at full ocean depth, including an overwater monitoring unit and an underwater measurement device, where the underwater measurement device includes an observation platform and a measuring mechanism carried on the observation platform; the observation platform includes a frame-type body and a floating body, a wing panel, a height measuring device, a floating ball cabin, a leveling mechanism, a counterweight, a release mechanism, and an underwater acoustic communication device mounted on the frame-type body; the height measuring device is used to detect the height of the underwater measurement device from the sea floor; the floating ball cabin is in the shape of a floating ball, for sealing a circuit system while providing buoyancy; the circuit system communicates with the overwater monitoring unit through the underwater acoustic communication device, for uploading the height of the underwater measurement device from the sea floor and measurement data of the mechanical properties; when the height of the underwater measurement device from the sea floor reaches a set height, the overwater monitoring unit issues a slow-descent instruction to control the wing panel to open outward relative to the frame-type body to reduce the descent rate of the underwater measurement device; when the underwater measurement device reaches the sea floor, the circuit system controls the leveling mechanism to adjust the orientation of the frame-type body, so that the frame-type body stands on the sea floor sediment stably; when the measurement operation is completed, the overwater monitoring unit issues a jettisoning instruction to control the release mechanism to discard the counterweight, and control the wing panel to close, so that the underwater measurement device ascends to the surface with the aid of the buoyancy of the floating body; the measuring mechanism includes one or more of a cone penetration measuring mechanism, a spherical penetration measuring mechanism, and a vane shear measuring mechanism for measuring the mechanical properties of the sea floor sediments, and/or a sampling mechanism for collecting a sample of the sea floor sediments.

Further, the observation platform is provided with a slow-descent cylinder; one end of the slow-descent cylinder is hinged to the frame-type body, and the other end is hinged to the wing panel; after receiving the slow-descent instruction or the jettisoning instruction issued by the overwater monitoring unit, the circuit system controls a piston rod of the slow-descent cylinder to extend or retract, so as to drive the wing panel to open or close.

Preferably, four wing panels are arranged around the periphery of the frame-type body; each wing panel is preferably hinged with two slow-descent cylinders. The configuration of two slow-descent cylinders can provide a greater driving force for the wing panel to overcome a greater seawater pressure and meet the needs of deep-ocean operations.

According to a preferred embodiment, the leveling mechanism is provided with multiple leveling legs and multiple leveling cylinders; the leveling legs are located on the bottom of the frame-type body, and each leveling leg is connected to a leveling cylinder; the floating ball cabin is provided with an attitude sensor, for detecting the orientation of the frame-type body, and generating attitude data to be sent to the circuit system; when the frame-type body reaches the sea floor, the circuit system controls the leveling cylinder to drive the leveling leg to extend or retract according to the received attitude data, so as to adjust the orientation of the frame-type body, making the frame-type body stably stand on the sea floor in a horizontal state.

According to another preferred embodiment, the release mechanism is provided with a release cylinder, a fixed pulley, a cable, and a hook; the fixed pulley is mounted on the frame-type body, and is wound with the cable; one end of the cable is connected to the release cylinder, and the other end is connected to the hook; in a default state, the hook extends into a lifting hole of the counterweight to hook the counterweight, so that the weight of the observation platform is increased, causing the underwater measurement device to descend to the sea floor; when the underwater measurement device is recovered, the circuit system controls the release cylinder to pull down the cable, which causes the hook to rotate under its weight and detach from the lifting hole of the counterweight, thereby separating the counterweight from the frame-type body to release the counterweight.

Preferably, the floating body includes a floating ball and a buoyancy board, which are mounted on top of the frame-type body; preferably, multiple floating balls are arranged in an array structure.

To facilitate a scientific research vessel to quickly search for the underwater measurement device emerging from the water, the frame-type body is further provided with an iridium beacon and an optical beacon on top. After the underwater measurement device emerges from the water, the iridium beacon sends a positioning signal to the overwater monitoring unit to inform the scientific research vessel of the geographic coordinates of the underwater measurement device. After the underwater measurement device emerges from the water, the optical beacon also automatically emits visible light to instruct the scientific research vessel to find the location of the underwater measurement device.

Preferably, the cone penetration measuring mechanism includes a bracket, a cone probe, a probe rod connected to the cone probe, and a penetration driving mechanism driving the probe rod to carry the cone probe up and down; the bracket is mounted on the frame-type body; the cone probe is internally provided with a pore water pressure sensor and a penetration resistance sensor.

Preferably, the spherical penetration measuring mechanism includes a bracket, a spherical probe, a probe rod connected to the spherical probe, and a penetration driving mechanism driving the probe rod to carry the spherical probe up and down; the bracket is mounted on the frame-type body; the spherical probe is internally provided with a pore water pressure sensor and a penetration resistance sensor.

Preferably, the vane shear measuring mechanism includes a bracket, a vane probe, a probe rod connected to the vane probe, a penetration driving mechanism driving the probe rod to carry the vane probe up and down, and a shear driving device driving the vane probe to rotate; the bracket is mounted on the frame-type body; the shear driving device is provided with a torque sensor for detecting a shear torque of the vane probe.

Preferably, the sampling mechanism includes a bracket, a sampling tube, a penetration driving mechanism driving the sampling tube up and down, and a hydraulic device extracting the sea floor sediment to the sampling tube; the bracket is mounted on the frame-type body.

Further, the circuit system includes a data acquisition unit, a control unit, a power drive unit, and a battery; the battery powers the data acquisition unit, the control unit, and the power drive unit; the data acquisition unit collects a sensing signal output by the pore water pressure sensor, the penetration resistance sensor and the torque sensor, and transmits the sensing signal to the control unit to calculate the mechanical properties of the sea floor sediment; the power drive unit is connected to the control unit, for generating a driving voltage required by the underwater measurement device.

Preferably, the penetration driving mechanism includes a penetration cylinder, a pulley block, a steel cable wound on the pulley block, and a slide plate pulled by the steel cable; the pulley block includes a fixed pulley block and a movable pulley block; the movable pulley block is connected to a piston rod of the penetration cylinder; the circuit system controls the piston rod of the penetration cylinder to extend or retract, so as to drive the movable pulley block up and down, thereby driving the steel cable to pull the slide plate up and down. The probe rod in the cone penetration measuring mechanism, the probe rod in the spherical penetration measuring mechanism, and the sampling tube in the sampling mechanism are fixedly mounted on the slide plate of the respective penetration driving mechanism, and are driven by the slide plate to insert into or recover from the sea floor sediment.

Preferably, the shear driving device includes a motor and a coupling; the motor is mounted on the slide plate of the penetration driving mechanism in the vane shear measuring mechanism, for receiving the driving voltage; a rotating shaft of the motor is connected to the probe rod of the vane probe through the coupling, for driving the vane probe to rotate to shear the sea floor soil, thereby achieving the measurement of the shear torque required to shear the soil.

Preferably, the hydraulic device includes a hydraulic cylinder and a sealing plug; the hydraulic cylinder is mounted on the slide plate of the penetration driving mechanism in the sampling mechanism; the sealing plug is located in the sampling tube, and connected to a piston rod of the hydraulic cylinder; the hydraulic cylinder is controlled by the circuit system to drive the sealing plug to move up, so as to reduce the air pressure in the sampling tube to extract sea floor sediment.

According to a preferred embodiment, to further increase the buoyancy of the measurement device, four floating ball cabins are mounted, and the data acquisition unit, the control unit, the power drive unit and the battery are accommodated in the four different floating ball cabins, respectively; each floating ball cabin is provided with a watertight connector, and a waterproof cable is connected between watertight connectors; circuits disposed in different floating ball cabins are electrically connected through the waterproof cable to transmit power and a signal.

To facilitate mounting of camera or video camera equipment, the floating ball cabin is preferably made of a transparent glass, and the floating ball cabin reserves a mounting space for a camera or a video camera. In this way, it is not necessary to additionally mount a special transparent box for sealing the camera or the video camera on the observation platform, thereby achieving the purpose of simplifying the structure, mounting and operation of the platform.

To reliably recover the underwater measurement device, the circuit system is programmed as follows. After the underwater measurement device completes the measurement operation and there is a delay for a period of time, if the jettisoning instruction issued by the overwater monitoring unit is not received, the underwater acoustic communication device is considered to be abnormal. At this time, the circuit system controls the release mechanism to discard the counterweight to perform the recovery operation by itself. If the circuit system fails to send a control signal to the release mechanism, a mechanical timing trigger device can also be set in the release mechanism. The mechanical timing trigger device starts timing when the underwater measurement device is launched, and automatically triggers the release mechanism to discard the counterweight when the timer reaches a set maximum time threshold. By adopting the above two alternative recovery strategies, the release mechanism can be controlled in a complementary way to ensure the reliable recovery of the underwater measurement device.

Compared with the prior art, the invention has advantages and positive effects. The system for measuring the mechanical properties of sea floor sediments can launch the underwater measurement device without a cable, and is therefore not restricted by the length of a cable. The working water depth can reach 11,000 m or more, so the measurement system can achieve in-situ measurement of the mechanical properties of the sea floor sediment at full ocean depth to meet various scientific research needs. In addition, by providing the slow-descent mechanism and the release mechanism on the underwater measurement device, the invention can ensure that the underwater measurement device descends and lands stably by itself. Further, the invention can also ensure that the underwater measurement device successfully achieves jettisoning for recovery by itself without the need for assistance by a scientific research vessel and a submersible. Therefore, the system can carry out a long-term continuous observation operation independently on the sea floor at any depth, providing a comprehensive guarantee for the effective implementation of marine research.

Other features and advantages of the invention will be better understood after reading the implementations of the invention described in detail with reference to the accompanying drawings.

DETAILED DESCRIPTION

The specific implementations of the invention are described below with reference to the accompanying drawings.

Figure 11:
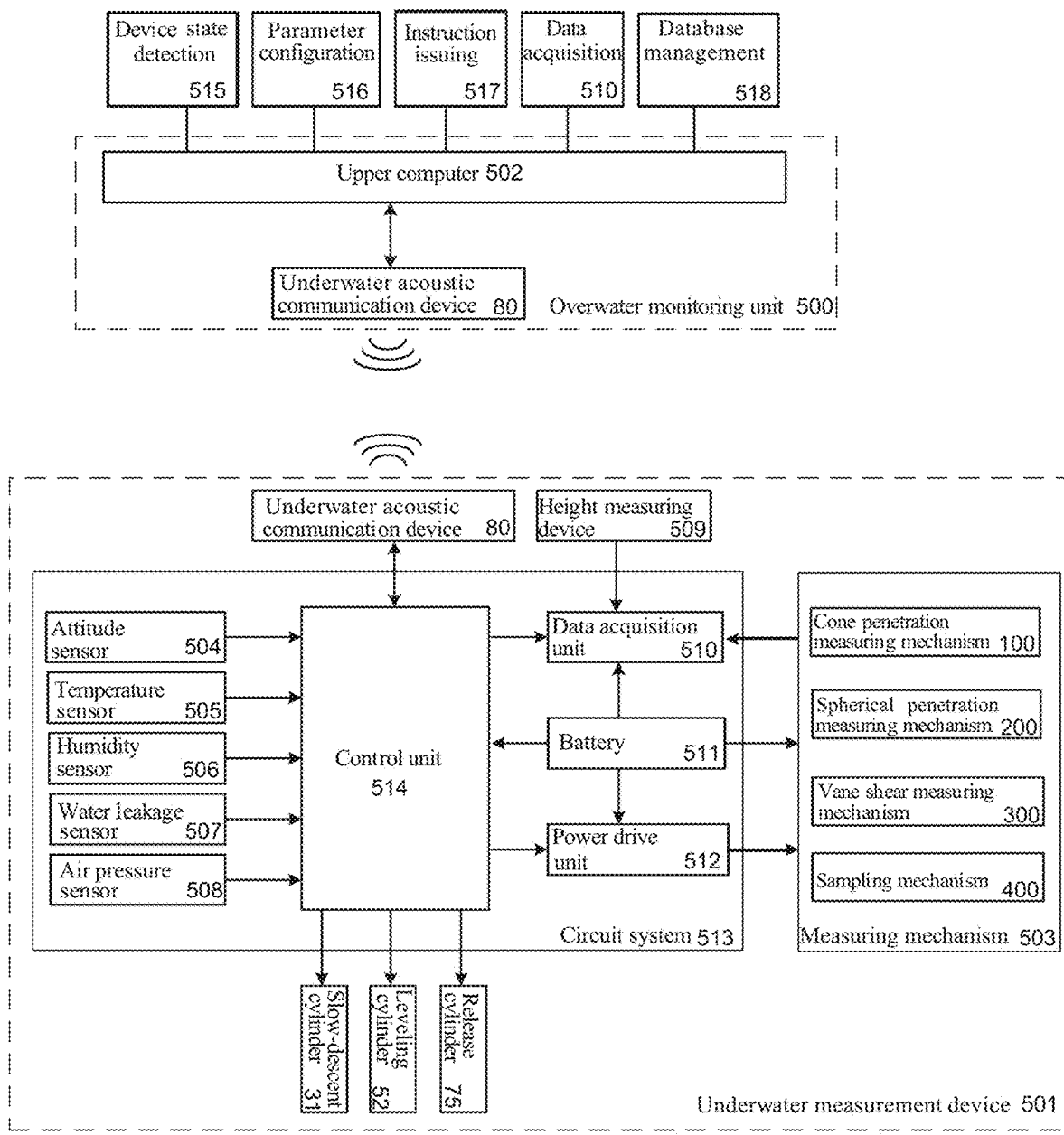
FIG. 11 is a functional block diagram of a circuit in an embodiment of a system for measuring the mechanical properties of sea floor sediments at full ocean depth proposed by the invention.

In a preferred embodiment, a system for measuring the mechanical properties of sea floor sediments includes two parts, namely an overwater monitoring unit 500 and an underwater measurement device 501, as shown in FIG. 11. The overwater monitoring unit 500 can be disposed on a scientific research vessel, including an upper computer 502 and an underwater acoustic communication device 80. The upper computer 502 communicates with the underwater measurement device 501 through the underwater acoustic communication device 80. The upper computer 502 realizes real-time monitoring of a trajectory of the underwater measurement device 501, a height from the sea floor 509, an underwater working environment 510, and a working state 515. The upper computer 502 sends a remote instruction 517 to control the underwater measurement device 501 to perform operations such as slow descent, penetration and recovery. Additionally, the upper computer 502 performs parameter configuration 516, as well as data processing, display and database storage and management of measurement data 518 of the mechanical properties of the sea floor sediments uploaded by the underwater measurement device 501. The underwater measurement device 501 is launched without a cable. The underwater measurement device 501 can descend to the sea floor at any depth by itself to measure the mechanical properties of the sea floor sediments, and ascend by itself for recovery after a measurement task is completed, thereby being reusable.

Figure 1:
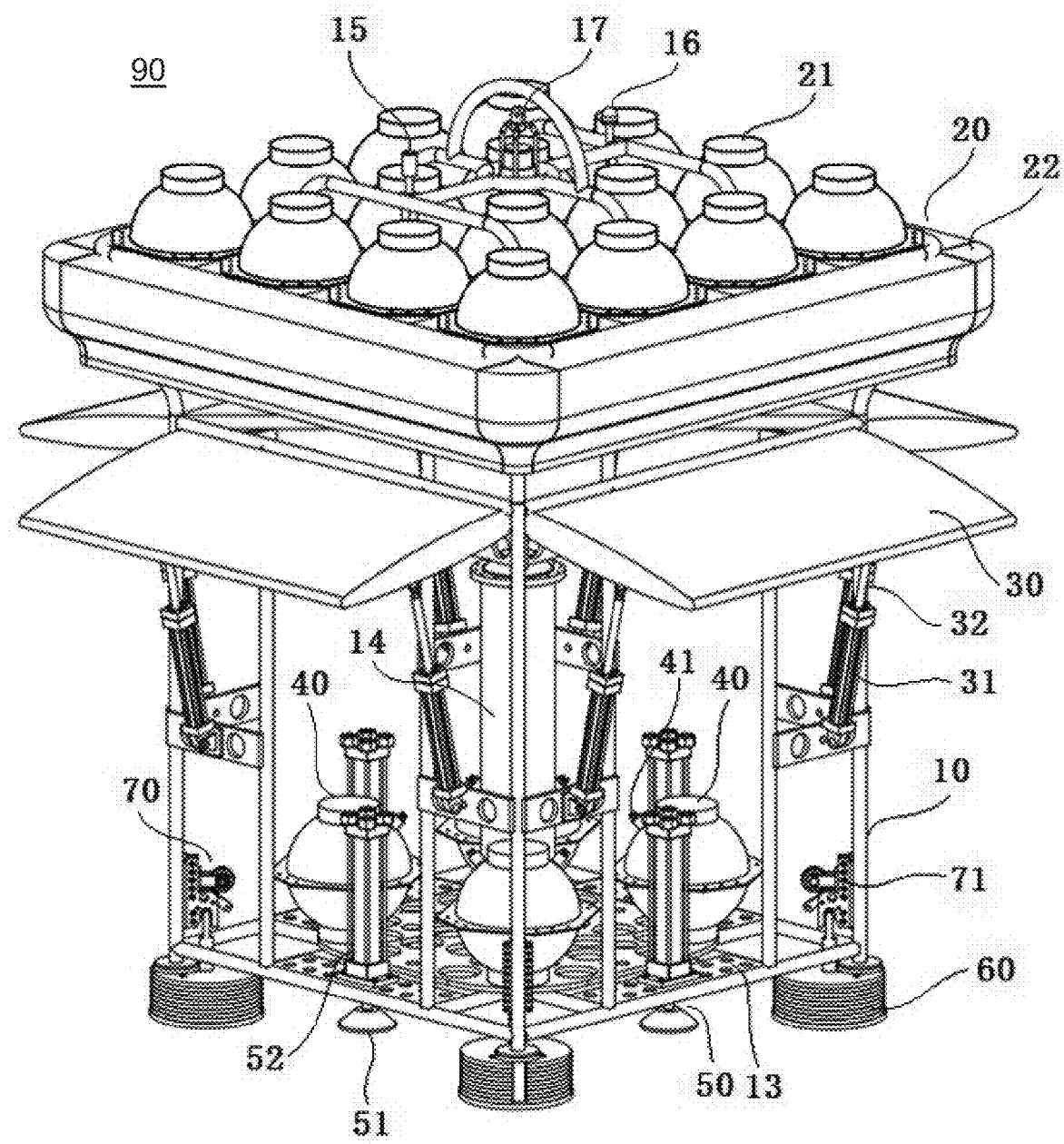
FIG. 1 is a schematic structural diagram of an embodiment of an observation platform in a system for measuring the mechanical properties of sea floor sediments at full ocean depth proposed by the invention.
Figure 5:
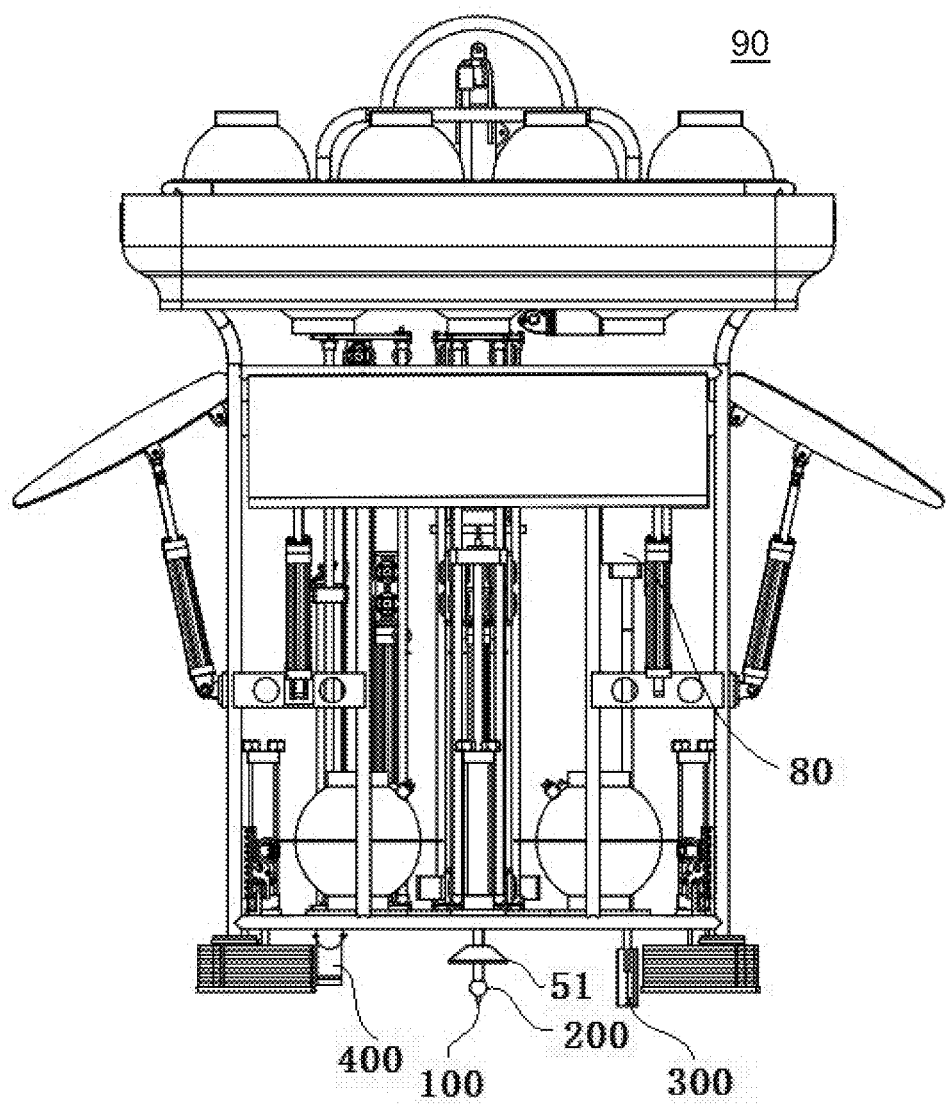
FIG. 5 is a schematic structural diagram of an embodiment of an underwater measurement device in a system for measuring the mechanical properties of sea floor sediments at full ocean depth proposed by the invention.

In another preferred embodiment, the underwater measurement device 501 is mainly composed of an observation platform 90 and a measuring mechanism 503 carried on the observation platform 90, as shown in FIG. 5. The observation platform 90 is a cableless sea floor observation platform 90, mainly composed of a frame-type body 10 and a floating body 20, a wing panel 30, a height measuring device, a floating ball cabin 40, a leveling mechanism 50, a counterweight 60, a release mechanism 70, an underwater acoustic communication device 80 and the like mounted on the frame-type body 10, as shown in FIGS. 1 and 5. The measuring mechanism 503 includes various measuring instruments for measuring the mechanical properties of sea floor sediments, including, but not limited to, one or more of a cone penetration measuring mechanism 100, a spherical penetration measuring mechanism 200, and a vane shear measuring mechanism 300, and may further include a sampling mechanism 400, for collecting samples of sea floor sediment to facilitate future laboratory research.

Figure 2:
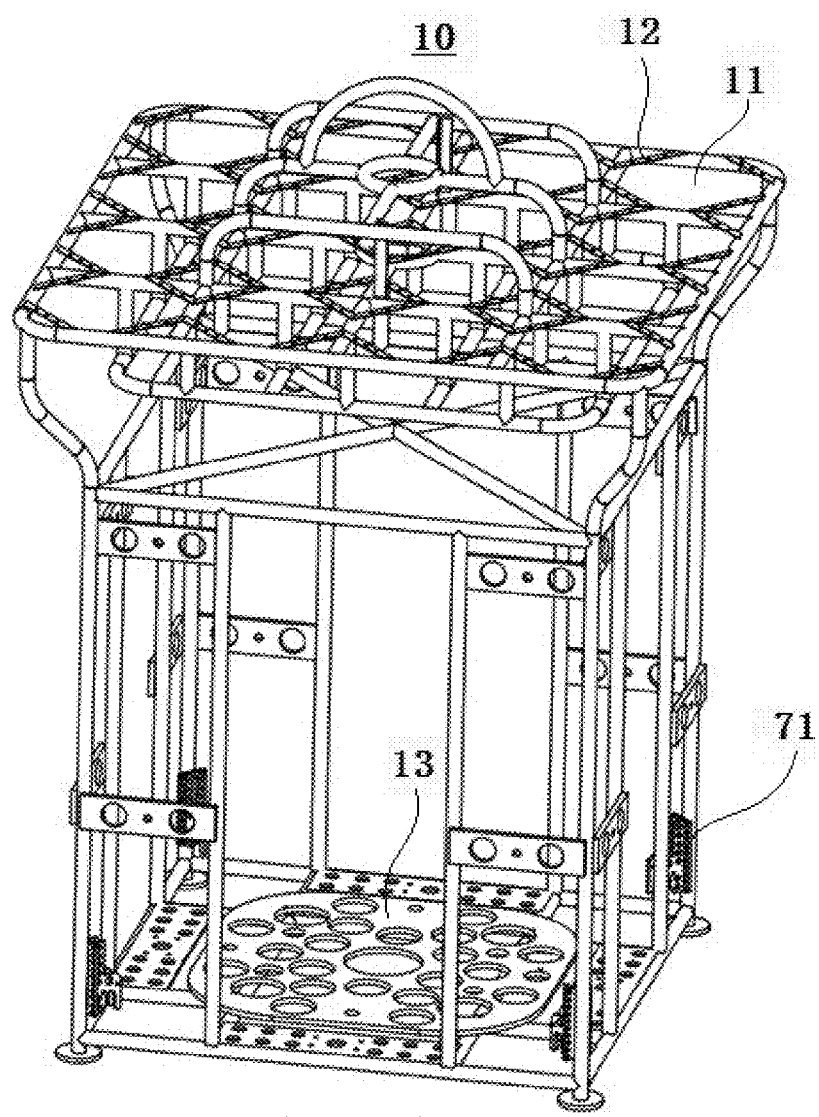
FIG. 2 is a schematic structural diagram of an embodiment of a frame-type body in FIG. 1.

In the observation platform 90, the frame-type body 10 is as a carrying body preferably made by welding a titanium alloy material and a high-strength aluminum alloy. While the carrying capacity and compressive strength are ensured, the overall weight of the carrying body 10 is reduced as much as possible, which is convenient for recovery. In preferred embodiment, the frame-type body 10 is preferably designed as a rectangular cage structure, as shown in FIG. 2, so as to mount different measuring mechanisms and observation equipment thereon. As a preferred mounting manner of preferred embodiment, the floating body 20 may be mounted on the top of the frame-type body 10 to provide sufficient upward buoyancy for the measurement device when the measurement device is recovered, so that the measurement device can ascend to the surface by itself. In preferred embodiment, the floating body 20 is preferably formed by combining a floating ball 21 and a buoyancy board 22. Specifically, a top surface of the frame-type body 10 may be designed in a rectangular grid shape, and each rectangular grid 11 is provided with a floating ball 21, such that the floating balls 21 are arranged as an array structure. Each rectangular grid 11 is welded with four assembly bars 12, and each of the assembly bars 12 forms a triangle with one of corners of the rectangular grid 11. Mounting the assembly bars 12 can both reinforce the rectangular grid 11 and facilitate the mounting and fixing of the floating ball 21 in the rectangular grid 11. The buoyancy board 22 wraps around the top of the frame-type body 10, which can increase the buoyancy and also cushion any forceful impact.

The wing panels 30 are mounted in a middle portion of the frame-type body 10, and are located below the buoyancy board 22. The distance between the wing panel 30 and the bottom of the frame-type body 10 is preferably ⅔ of the total height of the frame-type body 10, which can improve the stability of the mechanical structure. In preferred embodiment, four wing panels 30 are preferably mounted on the frame-type body 10, and are distributed around the frame-type body 10. Each wing panel 30 is designed as a streamlined wing surface, with an inner side hinged with the frame-type body 10. A slow-descent cylinder 31 is used to drive the wing panel 30 to open outward or close inward relative to the frame-type body 10. Specifically, one end (for example, the bottom of a cylinder barrel) of a slow-descent cylinder 31 is hinged to the frame-type body 10, and the other end (for example, a piston rod 32) is hinged to a bottom surface of the wing panel 30. The extension of the piston rod 32 of the slow-descent cylinder 31 can be controlled to drive the wing panel 30 to open, so as to reduce the descent rate of the measurement device. On the contrary, the retraction of the piston rod 32 of the slow-descent cylinder 31 can be controlled to pull the wing panel 30 back to reduce the descent resistance of the measurement device, allowing the measurement device to quickly descend to the sea floor. The slow-descent cylinder 31 is hinged to the frame-type body 10, so that the slow-descent cylinder 31 can automatically adjust an angle with the frame-type body 10 following the opening or closing of the wing panel 30, so as to adapt to the trajectory of the wing panel 30. The extension length of the piston rod 32 of the slow-descent cylinder 31 is adjusted according to a submerged depth of the measurement device. Accordingly, the opening angle of the wing panel 30 is adjusted, achieving the effect of multi-speed slow-descent, and achieving a stable landing of the measurement device on the ocean floor.

As the pressure on the sea floor is high during a deep-ocean operation, the wing panel 30 needs to overcome a large resistance to open. In a preferred embodiment, to ensure that the wing panel 30 can open reliably in a deep-ocean environment, each wing panel 30 is preferably provided with two slow-descent cylinders 31. As shown in FIG. 1, the two slow-descent cylinders 31 are hinged on left and right sides of a bottom surface of the wing panel 30, so as to provide a greater driving force for the wing panel 30.

An orifice plate 13 is mounted on the bottom of the frame-type body 10. As shown in FIG. 2, the orifice plate 13 is provided with several assembly holes of different sizes for mounting the floating ball cabin 40, the leveling mechanism 50, and the measuring mechanisms 100, 200, 300, 400.

In another preferred embodiment, to seal the circuit system 513 of the observation platform 90 and enable the circuit system 513 to adapt to the underwater working environment, a floating ball cabin 40 is designed to seal the circuit system 513. The floating ball cabin 40 is preferably made of a transparent glass. The floating ball cabin 40 is designed in the shape of a floating ball, and mounted on the orifice plate 13 on the bottom of the frame-type body 10. The cabin for enclosing the circuit system 513 is designed in a floating ball shape, which can provide auxiliary upward buoyancy for the measurement device while meeting an enclosing requirement. In addition, the floating ball cabin 40 is designed to be transparent. When it is necessary to mount camera or video camera equipment, a camera or a video camera can be directly disposed in the floating ball cabin 40 without additionally mounting a special box for enclosing the camera or the video camera on the observation platform 90. In this way, the floating ball cabin 40 achieves the purpose of simplifying the overall structure of the observation platform 90.

In another preferred embodiment, to obtain greater buoyancy, four floating ball cabins 40 are preferably mounted on the orifice plate 13 on the bottom of the frame-type body 10, for enclosing different functional circuits in the circuit system 513. With reference to FIG. 11, the circuit system 513 of the preferred embodiment mainly includes four parts: a data acquisition unit 510, a control unit 514, a power drive unit 512, and a battery 511. The four functional circuits are respectively placed into four different floating ball cabins 40 to form a data acquisition cabin, a control cabin, a power drive cabin and a battery cabin. Each floating ball cabin 40 is provided with at least one watertight connector 41. A waterproof cable (not shown) is connected between watertight connectors 41 on different floating ball cabins 40. The functional circuits disposed in the different floating ball cabins 40 are electrically connected through the waterproof cable to transmit power, an analog signal, and/or a digital signal.

The data acquisition cabin is mainly provided with data acquisition units, such as various interface boards, interface circuits and acquisition instruments. These data acquisition units are used to connect various measuring mechanisms carried on the observation platform 90, for collecting measurement data detected by the various measuring mechanisms, processing the data, and sending the data to the control unit 514 for data analysis and storage. In preferred embodiment, a height measuring device 509 is preferably independent of the circuit system 513. The height measuring device 509 is arranged on the frame-type body 10, and connected to the data acquisition unit 510. The height measuring device 509 may be an altimeter, an acoustic range finder, etc. The height measuring device 509 is used to detect the height of the frame-type body 10 from the sea floor, and generate a height detection signal to be sent to the data acquisition unit 510. The data is processed into a data format meeting a receiving requirement of the control unit 514 to be sent to the control unit 514, thereby realizing real-time monitoring of a descending position of the measurement device 501. The data acquisition cabin may also reserve a space for mounting a camera or a video camera. The data acquisition unit 510 acquires and sends image data captured by the camera or the video camera to the control unit 514.

The control cabin is mainly provided with a control unit 514 and sensing elements, such as an attitude sensor 504 (for example, a three-axis gyroscope, a three-axis accelerometer, and a three-axis electronic compass, etc.), a temperature sensor 505, a humidity sensor 506, an air pressure sensor 508, and a water leakage sensor 507, which are connected to the control unit 514. These sensing elements are used to detect an inclination angle of the observation platform 90 after landing and an environmental parameter in the floating ball cabin 40. The control unit 514 may include a controller (such as a central processing unit (CPU), a micro controller unit (MCU), and a digital signal processor (DSP)) and a memory. The controller serves as a control core of the entire circuit system 513 to perform coordinated control on each functional circuit, and send processed measurement data to memory for storage.

The power driving cabin is mainly provided with a power drive unit 512, for example, a motor drive circuit for driving a motor to operate. The motor drive unit is used to externally connect a measuring mechanism 503 carried on the observation platform 90. When it is necessary to control a motor in some measuring mechanisms 503 to operate, the control unit 514 can output a control signal to the power drive unit 512. Then, a driving voltage is generated to control the motor in the measuring mechanism 503 to operate to measure the mechanical properties of sea floor sediments or collect samples.

The battery cabin is mainly provided with a lithium battery and a seawater battery, for powering the observation platform 90 and the measuring mechanism 503 carried on the observation platform 90. The use of the seawater battery can meet the power demand of long-term continuous underwater operation of the measurement device.

In another preferred embodiment, in order for the observation platform 90 to stay horizontal after landing on the sea floor to ensure the accuracy of some measurement data, a leveling mechanism 50 is mounted on the bottom of the frame-type body 10, including a leveling leg 51 and a leveling cylinder 52, as shown in FIG. 1. In a preferred embodiment, four leveling cylinders 52 are arranged to control four leveling legs 51 to coordinate to adjust the balance of the frame-type body 10. Specifically, the leveling cylinder 52 may be mounted on the orifice plate 13 on the bottom of the frame-type body 10, with a piston rod facing downward, and connected to the leveling leg 51. The extension length of the piston rod of the leveling cylinder 52 is adjusted to change the attitude of the frame-type body 10 and adjust the frame-type body 10 to be horizontal.

A counterweight 60 is mounted on the bottom of the frame-type body 10; a release mechanism 70 is mounted on the frame-type body 10, and the release mechanism 70 hooks the counterweight 60. After the measurement device is put into the sea, the weight of the counterweight 60 is used to pull the measurement device down to descend onto the sea floor, so as to measure the mechanical properties of sea floor sediments. After the measurement operation is completed, the release mechanism 70 is controlled to discard the counterweight 60, so that the counterweight 60 is separated from the frame-type body 10. After that, the measurement device floats up with the aid of the floating ball 21, the buoyancy board 22, and the floating ball cabin 40, and ascends to the surface, to wait for the scientific research vessel to fish and recover it.

Figure 3:
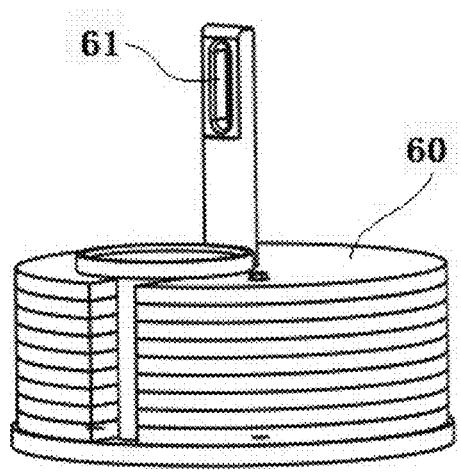
FIG. 3 is a schematic structural diagram of an embodiment of a counterweight in FIG. 1.
Figure 4:
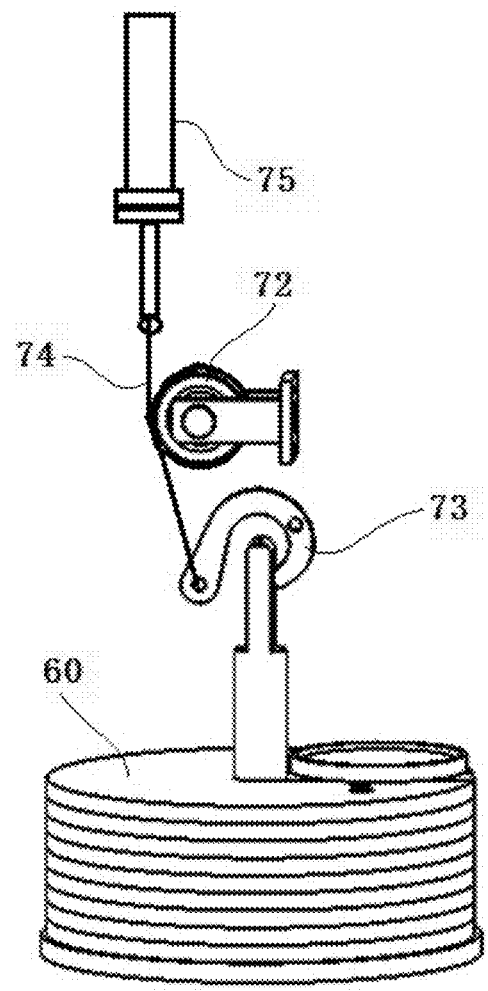
FIG. 4 is a schematic structural diagram of an embodiment of a counterweight and a release mechanism.

In another preferred embodiment of the release mechanism 70, a fixing bracket 71 is mounted on the frame-type body 10, as shown in FIG. 1. The fixing bracket 71 is provided with a fixed pulley 72 and a hook 73, as shown in FIG. 4. A cable 74 is wound around the fixed pulley 72, and one end of the cable 74 is connected to the hook 73, and the other end is connected to a release cylinder 75. The release cylinder 75 can be mounted on the frame-type body 10. A piston rod of the release cylinder 75 is controlled to extend or retract to pull the cable 74 up or down. In this way, the angle of the hook 73 is changed, and the counterweight 60 is hooked or released. Specifically, as shown in FIG. 3, the counterweight 60 can be provided with a lifting hole 61. In a default state, the release cylinder 75 controls the piston rod to retract to pull the cable 74 up, so that the hook 73 faces upward and extends into the lifting hole 61 of the counterweight 60 to lift the counterweight 60. When it is necessary to discard the counterweight 60, the release cylinder 75 is controlled to extend the piston rod thereof to pull down the cable 74. At this time, the hook 73 is rotated by a certain angle under the action of its own gravity, and detached from the lifting hole 61 of the counterweight 60 to release the counterweight 60, as shown in FIG. 4. Thereafter, the measurement device floats up with the aid of the floating body 20 and the floating ball cabin 40, and is recovered with the counterweight 60 discarded.

According to another preferred embodiment, the counterweight 60 and the release mechanism 70 are configured into four sets, which are arranged at four bottom corner positions of the rectangular frame-type body 10 to balance the down pull applied to the frame-type body 10. In this way, it is ensured that the attitude of the underwater measurement device 501 is stable during diving.

To provide hydraulic oil for the slow-descent cylinder 31, the leveling cylinder 52, and the release cylinder 75, a hydraulic station 14 is further mounted on the observation platform 90. As shown in FIG. 1, the hydraulic station 14 is preferably mounted at a center position of the orifice plate 13 on the bottom of the frame-type body 10, and communicates with the slow-descent cylinder 31, the leveling cylinder 52, and the release cylinder 75 respectively through different oil tubes. Each oil tube connected to each cylinder is provided with a solenoid valve. When a certain cylinder needs to be controlled to work, the solenoid valve on the oil tube connected to the controlled cylinder can be opened by the circuit system 513. Then the hydraulic station 14 is controlled to supply or pump the oil to the controlled cylinder to control a piston rod of the controlled cylinder to extend or retract, thereby meeting the working need of the controlled cylinder.

In addition, in another preferred embodiment, an iridium beacon 15 and an optical beacon 16 are further mounted on the top of the frame-type body 10, as shown in FIG. 1. The iridium beacon 15 can automatically transmit a positioning signal, for example, a global positioning system (GPS) signal to send geographic coordinates of the underwater measurement device 501 to the overwater monitoring unit 500, after the underwater measurement device 501 emerges from the water. This is convenient so that the scientific research vessel can quickly search for the underwater measurement device 501 in a sea area. After the underwater measurement device 501 emerges from the water, the optical beacon 16 can automatically transmit visible light to send a directional optical signal to the scientific research vessel, so that the scientific research vessel can find the location of the underwater measurement device 501. This can ensure safe and fast recovery of the underwater measurement device 501 even at night.

A lifting mechanism 17 is further mounted on the top of the frame-type body 10, which is used to cooperate with fishing equipment on the scientific research vessel, so as to facilitate the launching and fishing of the underwater measurement device 501. When the seawater in a sea area to be measured is not deep, a cable method can also be used to connect a cable on the scientific research vessel to the lifting mechanism 17 of the observation platform 90. The underwater measurement device 501 can be launched and recovered with the cable. Therefore, in a preferred embodiment, the underwater measurement device 501 supports both cabled and cableless launch, which extends the applicable field of the measurement system.

In another preferred embodiment, the underwater measurement device 501 can select multiple types of measuring mechanisms for measuring the mechanical properties of sea floor sediments. The various measuring mechanisms are mounted on the orifice plate 13 on the bottom of the frame-type body 10, and are controlled to penetrate into the sea floor sediment to detect the mechanical properties of sea floor sediments. In a preferred embodiment, the cone penetration measuring mechanism 100, the spherical penetration measuring mechanism 200, the vane shear measuring mechanism 300, and the sampling mechanism 400 carried on the observation platform 90 are described as examples, as shown in FIG. 5.

Figure 6:
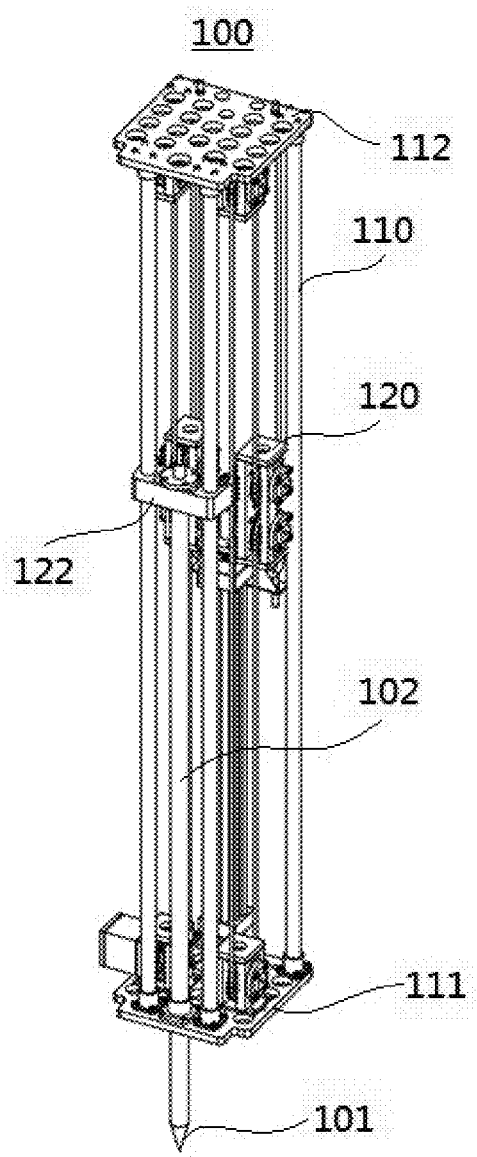
FIG. 6 is a schematic structural diagram of an embodiment of a cone penetration measuring mechanism in FIG. 5.
Figure 10:
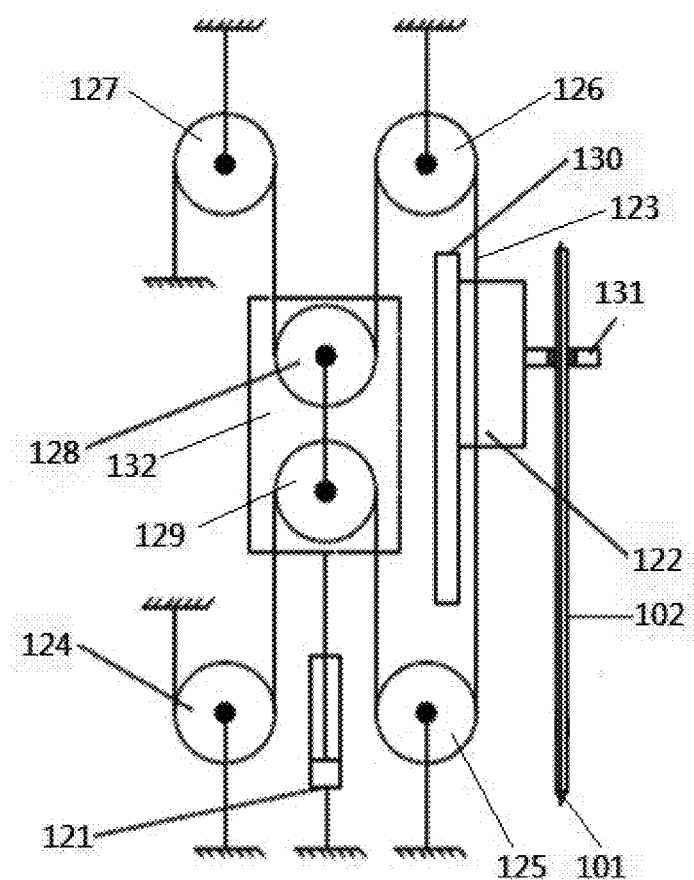
FIG. 10 is a schematic structural diagram of an embodiment of a penetration driving mechanism in FIG. 6.

In a preferred embodiment, the cone penetration measuring mechanism 100 mainly includes a bracket 110, a cone probe 101, a probe rod 102 connected to the cone probe 101, and a penetration driving mechanism 120 driving the probe rod 102 to carry the cone probe 101 up and down, as shown in FIG. 6. The bracket 110 is mounted on the frame-type body 10 of the observation platform 90, and the penetration driving mechanism 120 is mounted on the bracket 110. The penetration driving mechanism 120 includes a penetration cylinder 121, a slide plate 122, a pulley block, and a steel cable 123, etc., as shown in FIG. 6 and FIG. 10. The penetration cylinder 121 is mounted on a base 111 of the bracket 110. The pulley block includes a fixed pulley block and a movable pulley block. The movable pulley block is mounted on a carrying frame 132, and the carrying frame 132 is mounted on a piston rod of the penetration cylinder 121. The penetration cylinder 121 drives the movable pulley block up and down. The fixed pulley block includes four fixed pulleys. A first fixed pulley 124 and a second fixed pulley 125 are mounted on the base 111 of the bracket 110; a third fixed pulley 126 and a fourth fixed pulley 127 are mounted on a top plate 112 of the bracket 110. The movable pulley block includes two movable pulleys, that is, an upper movable pulley 128 and a lower movable pulley 129, which are axially connected and are in an up-down position relationship. The steel cable 123 is wound on the pulley block, and the winding order is: first fixed pulley 124→lower movable pulley 129→second fixed pulley 125→third fixed pulley 126→upper movable pulley 128→fourth fixed pulley 127. Two ends of the steel cable 123 are fixed on the bracket 110. The slide plate 122 is mounted on the steel cable 123, preferably on a steel cable located between the second fixed pulley 125 and the third fixed pulley 126. The steel cable 123 is used to pull the slide plate 122 up and down. In order to improve the movement stability of the slide plate 122, a guide rail 130 may be further mounted on the bracket 110. The guide rail 130 is used to support the slide plate 122, so that the slide plate 122 can move up and down along the guide rail 130. The slide plate 122 is provided with a clamping mechanism 131. The clamping mechanism 131 is used to clamp an upper half of the probe rod 102, so that the probe rod 102 can follow the slide plate 122 to move up and down. The cone probe 101 is mounted on a lower end of the probe rod 102, and the cone probe 101 extends beyond the base 111 of the bracket 110 with a cone head facing downward.

When it is necessary to use the cone penetration measuring mechanism 100 to measure the mechanical properties of sea floor sediments, the control unit 514 in the circuit system 513 outputs a control signal to control the hydraulic station 14 to provide the hydraulic oil for the penetration cylinder 121. In this way, the piston rod of the penetration cylinder 121 extends to control the movable pulley block to move up. When the lower movable pulley 129 is moved up, the steel cable 123 located between the second fixed pulley 125 and the third fixed pulley 126 is moved down, and drives the slide plate 123 to move down. Thus, the probe rod 102 is driven to descend with the cone probe 101 and penetrate into the sea floor sediment. The third fixed pulley 126 may be further provided with a displacement sensor (not shown), which detects a rotation angle of the third fixed pulley 126 for calculating a penetration depth of the cone probe 101 in the sea floor sediment. In a preferred embodiment, the data acquisition unit 510 in the circuit system 513 may be used to receive a detection signal output by the displacement sensor and to send the detection signal to the control unit 514. The control unit 514 calculates the penetration depth of the cone probe 101.

A pore water pressure sensor and a penetration resistance sensor can be enclosed inside the cone probe 102. During the penetration of the cone probe 102 into the sea floor sediment, the pore water pressure sensor detects the flow state of the sea floor sediment and the water pressure, and the penetration resistance sensor detects the resistance received by the cone probe 102. The pore water pressure sensor and the penetration resistance sensor send a generated sensing signal to the data acquisition unit 510 in the circuit system 513. The sensing signal is processed and transmitted to the control unit 514 to calculate the mechanical properties of the sea floor sediments. The specific calculation method is known, and will not be described in this embodiment. The control unit 514 combines the detection signals output by the displacement sensor, the pore water pressure sensor and the penetration resistance sensor to calculate the mechanical properties of the sea floor sediments at different depths.

After the mechanical property measurement is completed, the control unit 514 outputs a control signal to control the hydraulic station 14 to pump back the hydraulic oil. Thus, the piston rod of the penetration cylinder 121 is retracted to pull down the movable pulley block. The steel cable 123 between the second fixed pulley 125 and the third fixed pulley 126 pulls the slide plate 122 up. The probe rod 102 is driven to carry the cone probe 101 up to pull out from the sea floor sediment, and restore an original state, thereby completing the measurement task.

Figure 7:
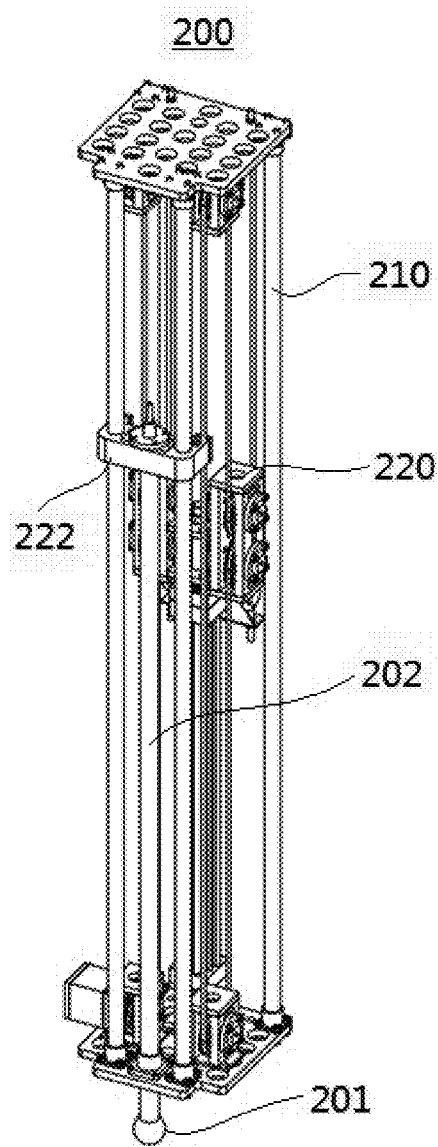
FIG. 7 is a schematic structural diagram of an embodiment of a spherical penetration measuring mechanism in FIG. 5.

In another preferred embodiment, the spherical penetration measuring mechanism 200 mainly includes a bracket 210, a spherical probe 201, a probe 202 connected to the spherical probe 201, and a penetration driving mechanism 220 driving the probe 202 to carry the spherical probe 201 up and down, as shown in FIG. 7. The spherical probe 201 is provided with a pore water pressure sensor and a penetration resistance sensor. The connection relationship of the components in the spherical penetration measuring mechanism 200, the specific structure and working principle of the penetration driving mechanism 220 are the same as those of the above-mentioned cone penetration measuring mechanism 100, and will not be further described in this embodiment.

Figure 8:
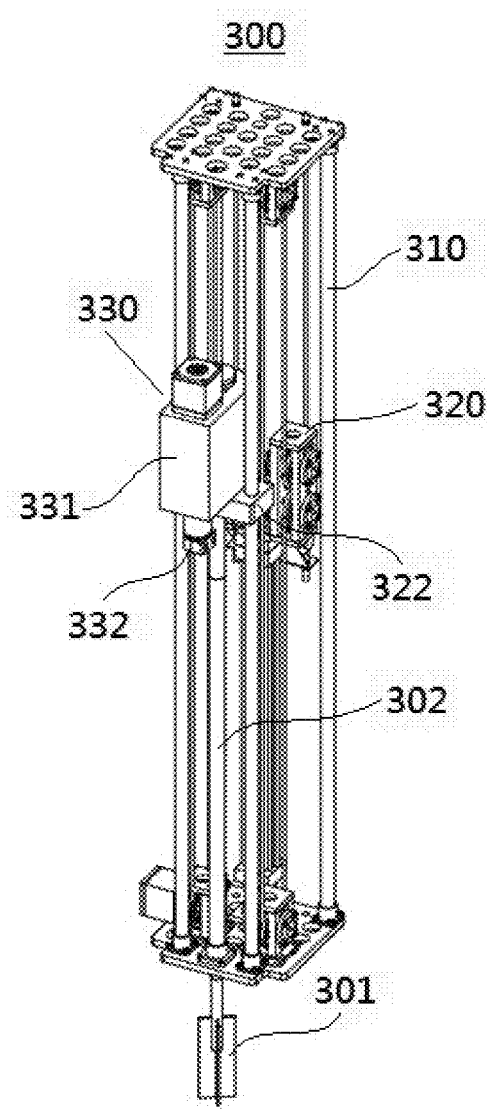
FIG. 8 is a schematic structural diagram of an embodiment of a vane shear measuring mechanism in FIG. 5.

In another preferred embodiment, the vane shear measuring mechanism 300 includes a bracket 310, a vane probe 301, a probe rod 302 connected to the vane probe 301, a penetration driving mechanism 320 driving the probe rod 302 to carry the vane probe 301 up and down, and a shear driving device 330 driving the vane probe 301 to rotate, as shown in FIG. 8. The bracket 310 is mounted on the frame-type body 10, and the penetration driving mechanism 320 is mounted on the bracket 310. The specific structure and working principle of the penetration driving mechanism 320 are the same as those of the penetration driving mechanism 120 in the above-mentioned cone penetration measuring mechanism 100, and will not be described in detail in this embodiment. The shear driving device 330 is mounted on the slide plate 322 of the penetration driving mechanism 320, and the shear driving device 330 is driven by the slide plate 322 to move up and down. The shear driving device 330 is provided with a motor 331 and a coupling 332. The motor 331 is mounted on the slide plate 322 and receives a driving voltage output by the power driving unit in the circuit system 513 to control the operation of the motor 331. A rotating shaft of the motor 331 is connected to the probe rod 302 through the coupling 332, so that the vane probe 301 is driven to rotate by the motor 331. The shear driving device 330 is provided with a torque sensor, for detecting a shear torque generated when the vane probe 301 rotates to destroy the soil structure of the sea floor sediment.

The working principle of the vane shear measuring mechanism 300 is as follows: first, the slide plate 322 in the penetration driving mechanism 320 is controlled by the control unit 514 in the circuit system 513 to carry the shear driving device 330 to move down; at the same time, the motor 331 in the shear driving device 330 is activated to drive the vane probe 301 to rotate, so that the vane probe 301 penetrates into the sea floor sediment while rotating. A displacement signal detected by the displacement sensor and a torque signal detected by the torque sensor are sent to the data acquisition unit 510 in the circuit system 513. The signals are processed by the data acquisition unit 510 and transmitted to the control unit 514 to calculate the mechanical properties of sea floor sediments at different depths.

Figure 9:
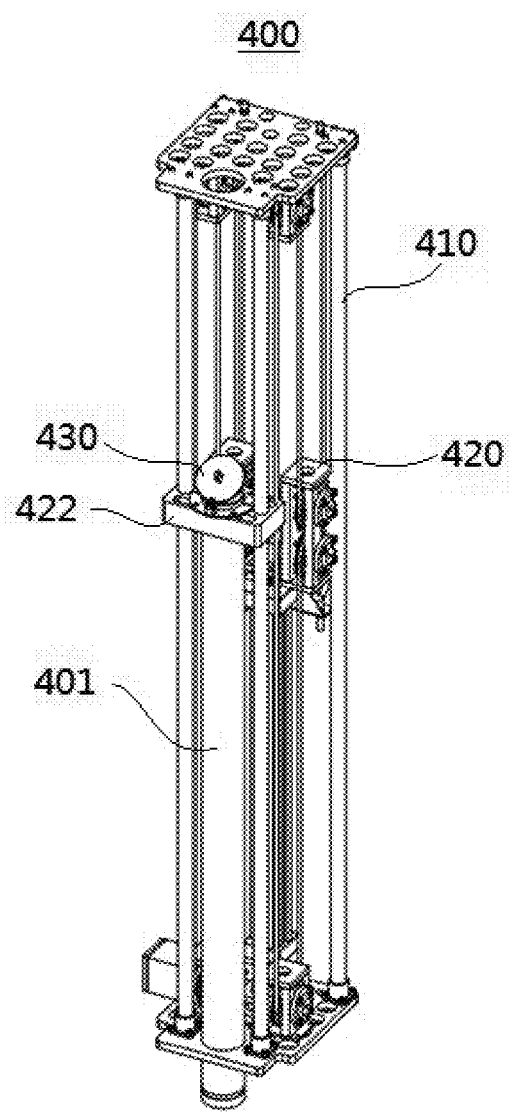
FIG. 9 is a schematic structural diagram of an embodiment of a sampling mechanism in FIG. 5.

In another preferred embodiment, the sampling mechanism 400 includes a bracket 410, a sampling tube 401, a penetration driving mechanism 420 driving the sampling tube 401 to move up and down, and a hydraulic device 430 extracting the sea floor sediment to the sampling tube 401, as shown in FIG. 9. The bracket 410 is mounted on the frame-type body 10, and the penetration driving mechanism 420 is mounted on the bracket 410. The specific structure and working principle of the penetration driving mechanism 420 are the same as those of the penetration driving mechanism 120 in the above-mentioned cone penetration measuring mechanism 100, and will not be described in detail in this embodiment. The hydraulic device 430 and the sampling tube 401 are mounted on a slide plate 422 of the penetration driving mechanism 420, and the hydraulic device 430 and the sampling tube 401 are driven by the slide plate 422 to move up and down. The hydraulic device 430 is provided with a hydraulic cylinder and a sealing plug. The hydraulic cylinder is mounted on the slide plate 422, and connected to the hydraulic station 14 through an oil tube. The sealing plug is placed in the sampling tube 401, and connected to a piston rod of the hydraulic cylinder.

When it is necessary to extract sea floor sediment, the penetration driving mechanism 420 is first controlled by the control unit 514 in the circuit system 513 to drive the sampling tube 401 to move down to penetrate into the sea floor sediment. Then, the hydraulic station 14 is controlled to drive the piston rod of the hydraulic cylinder to move the sealing plug up. Because a lower opening of the sampling tube 401 is penetrated into the sea floor sediment, the upward movement of the sealing plug will cause the volume of a space from the lower opening to the sealing plug in the sampling tube 401 to increase and the air pressure in the space to decrease. Thus, the sea floor sediment can automatically enter the sampling tube 401 under the influence of external pressure, so as to realize the collection of a sample of sea floor sediment.

In another preferred embodiment, the sampling tube 401 is designed to have a cylindrical shape. By penetrating into the sea floor sediment, the sampling tube can obtain an original sample of sediment, which is beneficial for indoor measurement in the future.

In another preferred embodiment, multiple types of measuring mechanisms 503 are carried on the observation platform 90. A suitable measuring mechanism 503 can be selected to mechanically measure different types of sediments, so as to meet the requirement of measuring the mechanical properties of different types of sediments. Moreover, different measuring mechanisms 503 can be used to mechanically measure sea floor sediments in the same area at the same time or at different time, so as to obtain multiple sets of measurement data for mutual verification. In this way, this embodiment improves the accuracy of the measurement result of the mechanical properties of sea floor sediments.

The specific working process of the system for measuring the mechanical properties of sea floor sediments in a preferred embodiment is described in detail below.

After the measurement system is carried by the scientific research vessel to reach a launch location in the sea area to be measured, the underwater measurement device 501 is lifted by an onboard steel cable and transferred to the sea surface. An unhooking device is controlled to detach the underwater measurement device 501, so that the underwater measurement device 501 descends into the sea.

After the underwater measurement device 501 descends into the sea, the circuit system 513 starts the height measuring device 509 to detect the height of the underwater measurement device 501 from the sea floor. The height measuring device 509 maintains communication with the overwater monitoring unit 500 through an underwater acoustic communication device 80. The underwater measurement device 501 descends with the aid of gravity and the counterweight 60. At an initial stage, the underwater measurement device 501 accelerates to dive. During the descent, under the influence of buoyancy, the underwater measurement device 501 gradually enters the state of constant-speed diving. During the dive of the underwater measurement device 501, the overwater monitoring unit 500 tracks the trajectory of the underwater measurement device 501 in real time through the underwater acoustic communication device 80, and feeds back information to the control unit 514 in the circuit system 513. The height measuring device 509 detects the height of the underwater measurement device 501 from the sea floor in real time, and transmits the height to the control unit 514. Then, the height is uploaded to the overwater monitoring unit 500 via the underwater acoustic communication device 80. When it is detected that the height of the underwater measurement device 501 from the sea floor reaches a set height, the overwater monitoring unit 500 issues a slow-descent instruction. After receiving the slow-descent instruction, the control unit 514 in the underwater measurement device 501 outputs a slow-descent control signal to control the piston rod 32 of the slow-descent cylinder 31 to extend. Thus, the wing panel 30 is pushed open to reduce the dive speed of the underwater measurement device 501. According to the change of the height of the underwater measurement device 501 from the sea floor, the opening angle of the wing panel 30 can be adjusted to realize multi-speed slow-descent. For example, when the underwater measurement device 501 is about 200 m away from the sea floor, the wing panel 30 can be controlled to open up to an angle of 45° with respect to the frame-type body 10. In this way, the dive speed of the underwater measurement device 501 is reduced, but is not too slow. When the underwater measurement device 501 is about 100 m away from the sea floor, the wing panel 30 can be controlled to further open up to an angle of 90° with respect to the frame-type body 10. In this way, the underwater measurement device 501 is controlled to dive slowly until landing stably.

After the underwater measurement device 501 lands stably on the sea floor, the control unit 514 detects the inclination angle of the frame-type body 10 after landing on the ocean floor through the attitude sensor 504. Then the control unit 514 outputs a leveling control signal to control the leveling cylinder 52 to drive the four leveling legs 51 to extend or retract until the frame-type body 10 is adjusted horizontally.

The overwater monitoring unit 500 issues a penetration instruction, and the control unit 514 in the underwater measurement device 501 receives the penetration instruction. Then the control unit 514 outputs a control signal to control one or more of the cone penetration measuring mechanism 100, the spherical penetration measuring mechanism 200, and the vane shear measuring mechanism 300 to operate. The probe of the controlled measuring mechanism 503 is penetrated into the sea floor sediment to measure the mechanical properties. Mechanical property data is collected, calculated, and uploaded to the overwater monitoring unit 500. At the same time, the control unit 514 controls the sampling mechanism 400 to collect a sample of the sea floor sediment.

After the underwater measuring mechanism 503 completes the measurement operation, the control unit 514 first controls the wing panel 30 to close, and then controls the release mechanism 70 to discard the counterweight 60. In this way, the underwater measurement device 501 floats up without power under the buoyancy of the floating body 20 and the floating ball cabin 40, thereby realizing recovery.

In order to ensure the reliable recovery of the underwater measurement device 501, this embodiment proposes three complementary release control schemes.

The first scheme is a main control scheme. The overwater monitoring unit 500 issues a jettisoning instruction after detecting that the underwater measurement device 501 has completed the measurement operations. The control unit 514 in the underwater measurement device 501 receives the jettisoning instruction through the underwater acoustic communication device 80. Then the control unit 514 generates a jettisoning control signal to control the release mechanism 70 to discard the counterweight 60.

The second scheme is a remedial scheme. If the underwater acoustic communication device 80 fails to normally communicate with the overwater monitoring unit 500 or the control unit 514, the control unit 514 will not be able to receive the jettisoning instruction issued by the overwater monitoring unit 500. In this situation, according to a preferred embodiment, the control unit 514 is set to reserve a waiting time (which can be specifically determined according to the actual situation) after the underwater measurement device 501 completes the measurement operation. After the waiting time is reached, if the control unit 514 still does not receive the jettisoning instruction issued by the overwater monitoring unit 500, the control unit 514 considers that the underwater acoustic communication device 80 has failed, and automatically generates a jettisoning control signal to control the release mechanism 70 to discard the counterweight 60 by itself.

The third scheme is another remedial scheme. A mechanical timing trigger device is set in the release mechanism 70, and a maximum time threshold is set in advance according to the actual working situation. When the underwater measurement device 501 is launched, the mechanical timing trigger device is turned on to record the working time of the underwater measurement device 501. When the timing reaches the set maximum time threshold, the circuit system 513 is considered abnormal for failing to send the jettisoning control signal normally. In this case, the mechanical timing trigger device can trigger the release mechanism 70 to discard the counterweight 60, ensuring the reliable recovery of the underwater measurement device 501. There are two ways to realize the triggering of the mechanical timing triggering device to the release mechanism 70. One way is that the mechanical timing triggering device, instead of the circuit system 513, is designed to generate the jettisoning control signal. The hydraulic station 14 is controlled to deliver the hydraulic oil to the release cylinder 75. In this way, the piston rod of the release cylinder 75 is controlled to extend, so that the hook 73 is detached from the counterweight 60 to release the counterweight 60. The other way is that the mechanical timing trigger device is designed to cut off the cable 74 when the timing reaches the set maximum time threshold, thereby achieving the release of the counterweight 60.

After the underwater measurement device 501 emerges from the water, the iridium beacon 15 and the optical beacon 16 are started to send geographic coordinates of the underwater measurement device 501 to the overwater monitoring unit 500, and emit light to guide the scientific research vessel to quickly find the location of the underwater measurement device 501. After the scientific research vessel arrives at the location of the underwater measurement device 501, a line throwing gun can be used to shoot a Kevlar® cable to connect the underwater measurement device 501, and fish and recover the underwater measurement device 501.

The underwater measurement device 501 of an embodiment has scientific and reasonable structure design. The underwater measurement device 501 can not only stably land as a whole, but also can be successful recovered. The underwater measurement device 501 can not only realize the measurement of the mechanical properties of sea floor sediments, but also can perform a long-term continuous observation operation of the sea floor environment, providing a comprehensive guarantee for the effective development of sea floor observations.

The above described is merely a preferred implementation of the invention. It should be pointed that a person of ordinary skill in the art may further make several improvements and modifications without departing from the principle of the invention, but such improvements and modifications should also be deemed as falling within the protection scope of the invention.

What is claimed is:

1. A system for measuring a mechanical property of a sea floor sediment at full ocean depth, comprising an overwater monitoring unit and an underwater measurement device, wherein the underwater measurement device comprises an observation platform and a measuring mechanism carried on the observation platform;

the observation platform comprises a frame-type body and a floating body, a wing panel, a height measuring device, a floating ball cabin, a leveling mechanism, a counterweight, a release mechanism, and an underwater acoustic communication device mounted on the frame-type body; wherein the height measuring device is used to detect a height of the underwater measurement device away from the sea floor;

the floating ball cabin is in a shape of a floating ball, for sealing a circuit system while providing buoyancy; the circuit system communicates with the overwater monitoring unit through the underwater acoustic communication device, for uploading the height of the underwater measurement device away from the sea floor and measurement data of the mechanical property;

four wing panels are mounted on the frame-type body, which are distributed around the frame-type body and are located below the floating body, and a distance between the wing panel and bottom of the frame-type body is $2/3$ of the total height of the frame-type body; each wing panel is designed as a streamlined wing surface, with an inner side hinged with the frame-type body; each wing panel is provided with two slow-descent cylinders which are hinged on left and right sides of a bottom surface of the wing panel, and one end of the slow-descent cylinder is hinged to the frame-type body, and the other end is hinged to a bottom surface of the wing panel; when the height of the underwater measurement device away from the sea floor reaches a set height, the overwater monitoring unit issues a slow-descent instruction to control the wing panel to open outward relative to the frame-type body, and to adjust an extension length of a piston rod of the slow-descent cylinder according to a submerged depth of the underwater measurement device, so that an opening angle of the wing panel is adjusted and the underwater measurement device is controlled to carry out multi-speed slow-descent until the measurement device lands on the ocean floor stably;

the leveling mechanism comprises multiple leveling legs and multiple leveling cylinders; the leveling legs are located on the bottom of the frame-type body, and each leveling leg is connected to a leveling cylinder; the floating ball cabin is provided therein with an attitude sensor, for detecting an attitude of the frame-type body, and generating attitude data to be sent to the circuit system; when the frame-type body reaches the sea floor, the circuit system controls the leveling cylinder to drive the leveling leg to extend or retract according to the received attitude data, so as to adjust the frame-type body, making the frame-type body stand horizontally on the sea floor;

when a measurement operation performed by the underwater measurement device is completed, the overwater monitoring unit issues a jettisoning instruction to control the release mechanism to discard the counterweight, and control the wing panel to close, so that the underwater measurement device ascends to the surface under the buoyancy of the floating body; the release mechanism comprises a release cylinder, a fixed pulley, a cable and a hook; the fixed pulley is mounted on the frame-type body, and is wound with the cable; one end of the cable is connected to the release cylinder, and the other end is connected to the hook; in a default state, the hook extends into a lifting hole of the counterweight to hook the counterweight, so that the weight of the observation platform is increased, causing the underwater measurement device to descend to the sea floor by itself; when the underwater measurement device is recovered, the circuit system controls the release cylinder to pull down the cable, which causes the hook to rotate under self-weight and detach from the lifting hole of the counterweight, thereby separating the counterweight from the frame-type body;

a hydraulic station is mounted at a center position of an orifice plate on the bottom of the frame-type body, and communicates with the slow-descent cylinder, the leveling cylinder, and the release cylinder respectively through different oil tubes; each oil tube connected to each cylinder is provided with a solenoid valve; when a certain cylinder needs to be controlled to work, the solenoid valve on the oil tube connected to the controlled cylinder can be opened by the circuit system, then the hydraulic station is controlled to supply or pump the oil to the controlled cylinder to control a piston rod of the controlled cylinder to extend or retract;

the measuring mechanism comprises one or more of a cone penetration measuring mechanism, a spherical penetration measuring mechanism, and a vane shear measuring mechanism for measuring the mechanical property of the sea floor sediment, and/or a sampling mechanism for collecting a sample of the sea floor sediment.

2. The system for measuring a mechanical property of a sea floor sediment at full ocean depth according to claim 1, wherein the floating body comprises a floating ball and a buoyancy board, which are mounted on a top of the frame-type body; the floating ball is multiple, arranged in an array structure.

3. The system for measuring a mechanical property of a sea floor sediment at full ocean depth according to claim 2, whereinafter the underwater measurement device completes the measurement operation and delays for a period of time, if the jettisoning instruction issued by the overwater monitoring unit is not received, the circuit system controls the release mechanism to discard the counterweight by itself;

the release mechanism is provided therein with a mechanical timing trigger device; the mechanical timing trigger device starts timing when the underwater measurement device is launched, and automatically triggers the release mechanism to discard the counterweight when the timing reaches a set maximum time threshold.

4. The system for measuring a mechanical property of a sea floor sediment at full ocean depth according to claim 1, wherein the frame-type body is further provided with an iridium beacon and an optical beacon on a top; after the underwater measurement device emerges from the water, the iridium beacon sends a positioning signal to the overwater monitoring unit, and after the underwater measurement device emerges from the water, the optical beacon automatically emits visible light.

5. The system for measuring a mechanical property of a sea floor sediment at full ocean depth according to claim 4, whereinafter the underwater measurement device completes the measurement operation and delays for a period of time, if the jettisoning instruction issued by the overwater monitoring unit is not received, the circuit system controls the release mechanism to discard the counterweight by itself;

the release mechanism is provided therein with a mechanical timing trigger device; the mechanical timing trigger device starts timing when the underwater measurement device is launched, and automatically triggers the release mechanism to discard the counterweight when the timing reaches a set maximum time threshold.

6. The system for measuring a mechanical property of a sea floor sediment at full ocean depth according to claim 1, wherein the cone penetration measuring mechanism comprises a bracket, a cone probe, a probe rod connected to the cone probe, and a penetration driving mechanism driving the probe rod to carry the cone probe up and down; the bracket is mounted on the frame-type body; the cone probe is internally provided with a pore water pressure sensor and a penetration resistance sensor;

the spherical penetration measuring mechanism comprises a bracket, a spherical probe, a probe rod connected to the spherical probe, and a penetration driving mechanism driving the probe rod to carry the spherical probe up and down; the bracket is mounted on the frame-type body; the spherical probe is internally provided with a pore water pressure sensor and a penetration resistance sensor;

the vane shear measuring mechanism comprises a bracket, a vane probe, a probe rod connected to the vane probe, a penetration driving mechanism driving the probe rod to carry the vane probe up and down, and a shear driving device driving the vane probe to rotate; the bracket is mounted on the frame-type body; the shear driving device is provided therein with a torque sensor for detecting a shear torque of the vane probe;

the sampling mechanism comprises a bracket, a sampling tube, a penetration driving mechanism driving the sampling tube up and down, and a hydraulic device extracting the sea floor sediment to the sampling tube; the bracket is mounted on the frame-type body;

the circuit system comprises a data acquisition unit, a control unit, a power drive unit, and a battery; the battery powers the data acquisition unit, the control unit, and the power drive unit; the data acquisition unit collects a sensing signal output by the pore water pressure sensor, the penetration resistance sensor and the torque sensor, and transmits the sensing signal to the control unit to calculate the mechanical property of the sea floor sediment; the power drive unit is connected to the control unit, for generating a driving voltage required by the underwater measurement device.

7. The system for measuring a mechanical property of a sea floor sediment at full ocean depth according to claim 6, wherein the penetration driving mechanism comprises a penetration cylinder, a pulley block, a steel cable wound on the pulley block, and a slide plate pulled by the steel cable; the pulley block comprises a fixed pulley block and a movable pulley block; the movable pulley block is connected to a piston rod of the penetration cylinder; the circuit system controls the piston rod of the penetration cylinder to extend or retract, so as to drive the movable pulley block up and down, thereby driving the steel cable to pull the slide plate up and down;

the probe rod in the cone penetration measuring mechanism, the probe rod in the spherical penetration measuring mechanism, and the sampling tube in the sampling mechanism are fixedly mounted on the slide plate of the respective penetration driving mechanism;

the shear driving device comprises a motor and a coupling; the motor is mounted on the slide plate of the penetration driving mechanism in the vane shear measuring mechanism, for receiving the driving voltage; a rotating shaft of the motor is connected to the probe rod of the vane probe through the coupling;

the hydraulic device comprises a hydraulic cylinder and a sealing plug; the hydraulic cylinder is mounted on the slide plate of the penetration driving mechanism in the sampling mechanism; the sealing plug is located in the sampling tube, and connected to a piston rod of the hydraulic cylinder; the hydraulic cylinder is controlled by the circuit system to drive the sealing plug to move up, so as to reduce the air pressure in the sampling tube to extract the sea floor sediment.

8. The system for measuring a mechanical property of a sea floor sediment at full ocean depth according to claim 7, whereinafter the underwater measurement device completes the measurement operation and delays for a period of time, if the jettisoning instruction issued by the overwater monitoring unit is not received, the circuit system controls the release mechanism to discard the counterweight by itself;

the release mechanism is provided therein with a mechanical timing trigger device; the mechanical timing trigger device starts timing when the underwater measurement device is launched, and automatically triggers the release mechanism to discard the counterweight when the timing reaches a set maximum time threshold.

9. The system for measuring a mechanical property of a sea floor sediment at full ocean depth according to claim 6, wherein four floating ball cabins are provided, the floating ball cabins are made of a transparent glass; and the floating ball cabins reserve a mounting space for a camera or a video camera; the data acquisition unit, the control unit, the power drive unit and the battery are accommodated in the four different floating ball cabins, respectively; each of the floating ball cabins is provided with a watertight connector, and a waterproof cable is connected between watertight connectors; circuits disposed in the different floating ball cabins are electrically connected through the waterproof cable.

10. The system for measuring a mechanical property of a sea floor sediment at full ocean depth according to claim 9, whereinafter the underwater measurement device completes the measurement operation and delays for a period of time, if the jettisoning instruction issued by the overwater monitoring unit is not received, the circuit system controls the release mechanism to discard the counterweight by itself;

the release mechanism is provided therein with a mechanical timing trigger device; the mechanical timing trigger device starts timing when the underwater measurement device is launched, and automatically triggers the release mechanism to discard the counterweight when the timing reaches a set maximum time threshold.

11. The system for measuring a mechanical property of a sea floor sediment at full ocean depth according to claim 6, whereinafter the underwater measurement device completes the measurement operation and delays for a period of time, if the jettisoning instruction issued by the overwater monitoring unit is not received, the circuit system controls the release mechanism to discard the counterweight by itself;

the release mechanism is provided therein with a mechanical timing trigger device; the mechanical timing trigger device starts timing when the underwater measurement device is launched, and automatically triggers the release mechanism to discard the counterweight when the timing reaches a set maximum time threshold.

12. The system for measuring a mechanical property of a sea floor sediment at full ocean depth according to claim 1, whereinafter the underwater measurement device completes the measurement operation and delays for a period of time, if the jettisoning instruction issued by the overwater monitoring unit is not received, the circuit system controls the release mechanism to discard the counterweight by itself;
 the release mechanism is provided therein with a mechanical timing trigger device; the mechanical timing trigger device starts timing when the underwater measurement device is launched, and automatically triggers the release mechanism to discard the counterweight when the timing reaches a set maximum time threshold.

* * * * *